United States Patent [19]

Johnson et al.

[11] Patent Number: 5,278,046

[45] Date of Patent: Jan. 11, 1994

[54] SOYBEAN PEROXIDASE ASSAYS

[75] Inventors: Mark A. Johnson, Chillicothe; Alexander R. Pokora, Pickerington, both of Ohio

[73] Assignee: The Mead Corporation, Dayton, Ohio

[21] Appl. No.: 760,870

[22] Filed: Sep. 16, 1991

[51] Int. Cl.⁵ .................. G01N 33/536; G12N 9/96
[52] U.S. Cl. .................. 435/7.9; 435/7.94; 435/7.95; 435/28; 435/188; 435/805; 435/970; 435/975
[58] Field of Search ............ 435/7.94, 7.9, 7.95, 435/28, 188, 192, 805, 970, 975

[56] References Cited

U.S. PATENT DOCUMENTS 5,147,793  9/1992  Johnson et al. .................. 435/192

OTHER PUBLICATIONS

Avrameas, S. "Immunoenzyme Techniques: Enzymes as Markers for the Localization of Antigens and Antibodies." *Intl. Rev. of Cytol.* 27:349–385 (1970).

Saunders et al. *Peroxidase.* Butterworth, Inc., Wash. D.C. (1964) pp. 2–3, 40–41, 61.

Harlow and Lane, "Labeling-Antibodies" (ch. 9) in *Antibodies, A Laboratory Manual* (1988, Cold Spring Harbor Laboratory) pp. 342–345.

*Primary Examiner*—Mary E. Ceperley
*Attorney, Agent, or Firm*—Thompson, Hine and Flory

[57] ABSTRACT

An analytical composition comprising antibody conjugate, an indicator which is capable of providing a detectable condition in the presence of peroxidase and hydrogen peroxide assays performed using this composition are described.

13 Claims, No Drawings 4,278,046

SOYBEAN PEROXIDASE ASSAYS

BACKGROUND OF THE INVENTION

The invention relates to medical and environmental diagnostics employing soybean peroxidase in place of horseradish peroxidase which has been historically used.

Enzymes are now widely used in medical and environmental diagnostics. Horseradish peroxidase has been one of the most satisfactory enzymes but is relatively expensive. It has now been found that soybean peroxidase can be readily harvested from soybean hulls at minimal expense and be substituted for horseradish peroxidase in these diagnostic chemistries.

Several diagnostic chemistries using the enzymatic activity of horseradish peroxidase have been described in the literature. Horseradish peroxidase has been used for diagnostic determinations of various analytes and has been used as a label in enzyme labeled antibodies used in the determination of immunologically reactive species (i.e. immunoassays) Such determinations can be carried out in solution or in dry analytical elements.

One type of useful assay utilizes enzymatic reactions wherein the analyte, upon contact with the appropriate reagents, reacts with oxygen in the presence of a suitable enzyme to produce hydrogen peroxide in proportion to the concentration of the analyte. A detectable product such as a visible or fluorescent dye is then produced by the reaction of hydrogen peroxide in proportion to the concentration of the analyte in the tested liquid Peroxidase is generally used in such assays to catalyze the oxidation of the interactive composition by hydrogen peroxide One example of such an assay is a glucose assay using glucose oxidase Glucose is oxidized in the presence of oxygen by the enzyme, glucose oxidase, to produce glucolactone and hydrogen peroxide. In the presence of peroxidase, the hydrogen peroxide oxidizes a colorless dye such as tetramethylbenzidine to produce a colored product.

Another type of assay utilizes an immunologically reactive compound such as an antibody. These chemistries can be generally classified into two groups, namely, conjugate or enzyme labeled antibody procedures, and non-conjugate or unlabeled antibody procedures. In the conjugate procedures, the enzyme is covalently linked to the antibody and applied to a sample containing the immobilized antigen to be detected. Thereafter the enzyme substrate, e.g., hydrogen peroxide, and an oxidazable chromogen such as a leuco dye are applied. In the presence of the peroxidase, the peroxide reacts with the chromogen resulting in the production of color. The production of color indicates the presence and in some cases the amount of the antigen. In another method, a competing substance is used to dislodge an antibody enzyme conjugate from an immobilized substrate, leading to an absence of color.

In a method sometimes referred to as the sandwich assay or enzyme linked immunoadsorbent assay (ELISA), a first antibody is bound to a solid support surface and challenged with a fluid sample suspected to contain the antigen to be detected and an enzyme-antibody conjugate. The antigen complexes with the antibody and the conjugate bonds to the antigen. Subsequent introduction of the substrate and chromogen produces a visual indication of the presence of the antigen.

Procedures employing non-conjugated enzymes include the enzyme bridge method and the peroxidase-antiperoxidase method. These methods use an antiperoxidase antibody produced by injecting peroxidase into an animal such as a goat, rabbit or guinea pig. The method does not require chemical conjugation of the antibody to the enzyme but consists of binding the enzyme to the antigen through the antigen-antibody reaction of an immunoglobulin-enzyme bridge. In the enzyme bridge method a secondary antibody acts as an immunologic bridge between the primary antibody against the suspected antigen and the antiperoxidase antibody. The antiperoxidase antibody in turn binds the peroxidase which catalyzes the indicator reaction. In the peroxidase-antiperoxidase method, a complex of the peroxidase and the antiperoxidase antibody is formed. This complex can then be used in the immunologic bridge method.

SUMMARY OF THE INVENTION

The present invention advocates the use of soybean peroxidase in place of horseradish peroxidase in the medical and environmental diagnostics.

Preliminary studies indicate that the specific activity of soybean peroxidase from commercial hulls is much higher than horseradish peroxidase. In addition, the rate of oxidation of phenols under identical conditions is faster with soybean peroxidase than horseradish peroxidase. This indicates that less effort should be required to purify the enzyme for diagnostic applications and that higher sensitivities should be obtained with the enzyme. Studies also indicate that temperature can be increased to accelerate soybean peroxidase oxidations to a higher rate and that certain denaturants such as certain solvents do not interfere with the soybean enzyme as much as they do with the horseradish enzyme. This indicates that diagnostic coupled reactions, such as the diagnosis of glucose, can be performed under conditions where horseradish peroxidase would otherwise fail or show reduced sensitivity.

One manifestation of the invention is an analytical composition comprising soybean peroxidase or a soybean peroxidase-antibody conjugate, an indicator which is capable of providing a detectable condition indicating the presence of peroxidase and a peroxide.

Another manifestation of the invention is soybean peroxidase-antibody conjugates Soybean peroxidase is a glyco-protein and commonly used chemistries provide a synthetic route to protein linked peroxidase enabling the linkage of soybean peroxidase to avidin, IgG immunogloglobulins and ferritin.

Another manifestation of the invention is anti-soybean peroxidase-antibody soybean peroxidase complexes.

Another manifestation of the invention is anti-soybean peroxidase antibody.

Also provided is a method for the determination of an analyte comprising the steps of contacting a sample suspected of containing an analyte with soybean peroxidase or a soybean peroxidase-labeled antibody, an indicator which is capable of providing a detectable change in the presence of peroxidase and hydrogen peroxide, and determining said detectable change as a result of the presence of said analyte.

Still another manifestation of the invention is a method for detecting an antigen which includes the step of adding soybean peroxidase to a sample suspected of containing the antigen to be detected under conditions such that said peroxidase directly or indirectly bonds to said antigen via an antibody and adding a substrate for said peroxidase and a chromogen to said sample under conditions such that said peroxidase and said substrate react with said chromogen and produce a change in color which is an indication of the presence and/or amount of said antigen.

This invention also provides an analytical element comprising an absorbent carrier material containing peroxidase or a peroxidase-labeled antibody, a leuco dye (or other indicator) which is capable of providing a detectable dye in the presence of peroxidase and hydrogen peroxide or another peroxide.

DETAILED DESCRIPTION OF THE INVENTION

Enzyme assays in accordance with the invention are performed using reagents, reaction conditions and techniques previously used for horseradish peroxidase assays with the exception that soybean peroxidase is substituted for horseradish peroxidase.

The invention can be used to assay biological fluids of either animals or humans. Such fluids include, but are not limited to, whole blood, plasma, sera, lymph, bile, urine, spinal fluid, sputum, perspiration and the like as well as stool secretions. It is also possible to assay fluid preparations of human or animal tissue such as skeletal muscle, heart, kidney, lungs, brains, bone marrow, skin and the like. The invention can also be used to assay plant tissues, drugs (C&E News, Jul. 8, 1991) and to assay antibodies used to characterize binding surfaces such as paper fibers (Nordic Pulp and Paper Res. J., pp. 152-55, 1988).

Among the analytes which can be assayed in accordance with the invention are hydrogen peroxide, analytes which are capable of producing hydrogen peroxide (i.e. they can participate in one or more reactions which produce hydrogen peroxide in the presence of suitable interactive compositions) such as glucose, triglycerides, uric acid, cholesterol, galactose, amino acids, creatine kinase, pyruvate, and others known to one skilled in the art, and immunologically reactive ligands which are substances that will complex specifically with a corresponding receptor such as an antibody Such ligands include, but are not limited to, antigens, haptens (e.g., peptidehormones, insecticides, nonpeptide hormones, carbohydrates (e.g., glucose, maltose, lactose), coenzymes, catecholamines, vitamins and cofactors, lipids, drugs, steroids, toxins, nucleic acid constituents, carcinogens, plant hormones, etc.), antibodies, therapeutic drugs, proteins, virus antigens, bacteria, peptides, etc.

Antigens detectable using the assays of the present invention include: ferritin, testosterone, estrogen, insulin, a-1-fetoprotein, aldosterone, 17-hydroxyprogesterone, human chorionic gonadotropin (HCG), acetyl choline receptor, a-bungarotoxin, low density lipoprotein, high density lipoprotein, plague capsular antigen, diosgenin, digoxin, abscisic acid, tuberculosis organism, protein C - blood coagulation factor XIV, seed globulins, a-amylase, b-2-macroglobulin, myelin basic proteins, n. gonorrhoeae, cocaine, tetrahydrocannabinol, HIV capsular proteins, and others.

Enzyme antibody conjugates in accordance with the invention may be prepared by the method of Avrameas, S., Immunoenzyme Techniques: Enzymes as Markers for the Localization of Antigens and Antibodies. *Int Rev Cytol* 1970;27:349, or the method of Nakane P. K., Application of Peroxidase-labeled Antibodies to the Intracellular Localization of Hormones, *Acta Endocrinol* 1971;153(suppl):1901; Nakan, P. K., Pierce, G. B. Jr., Enzyme-labeled Antibodies: Preparation and Application for the Localization of Antigens, *J. Histochem Cytochem* 1966;14:929-931: Nakane, P. K., Pierce, G. B. Jr., Enzyme-labeled Antibodies for the Light and Electron Microscopic Localization of Tissue Antigens, *J Cell Biol* 1967;33:307.

Soy peroxidase-antibody complexes may be complexes of polyclonal or monoclonal antibodies. They may be prepared by the process described by Sternberger, L. A, Hardy, P. H. Jr., Cuculis, J. J., et al: The Unlabeled Antibody-Enzyme Method of Immunohistochemistry Preparation and Properties of Soluble Antigen-antibody Complex (Horseradish Peroxidase-Antihorseradish Peroxidase) and Its Use in Identification of Spirochetes, *J Histochem Cytochem* 1970;18:315. More particularly, the antiserum to soybean peroxidase can be prepared by a series of injections of the enzyme into young albino rabbits or young guinea pigs. For example, a first sensitizing dose of 4 mg purified soybean peroxidase may be dissolved in a 1 ml saline and 1 ml complete Freund's adjuvent and injected subcutaneously in 0.5 ml aliquots. Four weeks and eight weeks later 2 mg of the peroxidase may be dissolved in saline and injected intravenously. Four days later blood may be drawn. In order to introduce the enzyme label, the serum is incubated with a solution of the peroxidase.

Soybean peroxidase from any of a variety of soybeans may be used in the present invention. In a particularly preferred embodiment, Williams 82 variety seed hulls are used. The occurrence of a single isozyme of soybean peroxidase in Williams 82 variety seed hulls has been reported by Gillikin and Graham, *Plant Physical* (A Supp.):53 (1989). Considerable effort has been expended in the isolation of specific horseradish isozymes to achieve uniform and reproducible diagnostic products. The high enrichment of a single isozyme in hulls from Williams 82 variety soybeans reduces or eliminates the need for isozyme purification.

In Table 1 below, the soybean peroxidase yield and activity from various sources is tabulated.

TABLE 1

| Peroxidase from Different Sources | | | |
|---|---|---|---|
| SOURCE | FORM | PEROXIDASE YIELD U/g hull fresh wt. | ACTIVITY* U/mg protein |
| J. R. Kelly | Frey variety bean | 90 | 33 |
| Agri Services | Williams variety bean | 150 | 64 |
| Process Mixing | Williams variety hulls (wet) | .83 | 8 |
| Cargill | Mixed variety ground hulls | 100 | 55 |
| Central Soya | | | |
| August | Mixed variety whole hulls | 100 | 61 |
| December | | 300 | 134 |
| January | Mixed variety ground hulls | 220 | 32 |
| J. R. Kelly | Whole horseradish roots | 40 | 25 |

The table shows that high peroxidase activity can be obtained from commercial soybean processors. The most important factors determining peroxidase value are the age of the beans at the time of dehulling and the amount of contaminating bean material. As a general rule, the sooner the beans are dehulled after harvest, the greater is the yield and activity. Hulls from beans over one year old have been found not to have acceptable peroxidase levels in some cases.

Soybean peroxidase can be harvested from soybean hulls by the method described in commonly assigned U.S. application Ser. No. 07/599,584 filed Oct. 18, 1990, now U.S. Pat. No. 5,147,793 application Ser. No. 07/699,905 filed May 14, 1991. Soy peroxidase, being water soluble, is easily harvested by homogenizing the protein source with water, filtering the homogenate, and retaining the filtrate.

In accordance with a preferred purification technique described in U.S. application Ser. No. 07/699,905 filed May 14, 1991, the homogenate is frozen and thawed to accelerate separation of the homogenate. The freeze-thaw treatment accelerates sedimentation and clarification of the extract and often makes it unnecessary to use detergents and protein fixatives to purify the enzyme.

High speed emulsifiers or a Netzsch Mill provide a good yield of peroxidase. The disadvantage of an emulsifier is that the resulting colloid is difficult to separate. Alternate homogenization techniques include wet or dry milling in an attritor followed by water extraction. The degree of homogenization is adjusted to facilitate separation. If the soybean hull is homogenized to a thick paste, it becomes too difficult to separate.

The attritor media affects yield and grind time. Preliminary studies indicate that zirconium oxide gives the best time and yield performance. This may be due to the fact that zirconium oxide is an inert media which does not contribute metals to the extract and that higher density compared to ceramic gives more efficient grinding.

The filtrate may be treated to remove proteinaceous and lipophilic impurities by adding to the filtrate a solution of a protein fixative or a detergent and forcing the enzyme to precipitate by the addition of a non-solvent for the peroxidase such as acetone or isopropanol. The protein fixative and detergent both preferentially render the protein contaminants insoluble in water. The detergent also insolublizes non-protein lipophilic impurities. After addition of the fixative or detergent, a non-solvent for peroxidase is added to the solution to force the peroxidase and impurities to precipitate. The precipitate is separated, water is added to redissolve preferentially the peroxidase and the sample is centrifuged. The peroxidase is recovered as the supernatant solution. While these treatments probably do not completely remove impurities, they reduce them to a level that the oxidation product obtained using the peroxidase is improved in quality.

When using the detergent, the precipitate is preferably treated with a solution of phenol and a small amount of hydrogen peroxide. This appears to cause the phenol to interact with the detergent and enhance the binding of the impurities. After about one hour the sample is centrifuged to remove the impurities. The peroxidase is recovered in the supernatant solution. These processes may be repeated to further purify the enzyme.

The protein fixatives useful in treating the peroxidase include tannic acid, tannins, monolignols, fulvic acids, lignan, humic acids, melanoidins, proanthcyanidins, stilbenes, depsides, lignin model compounds, soluble suberin, flavonoids, soluble lignin, dihydroxyphenyl compounds, kerogen, gallic acid esters, phenolic acids, gallic acid amides, dihydric phenols, hexahydroxydiphenic glucose esters, polymeric phenols, bis (hydroxyphenyl) sulfones, bitumens, soluble lignite extracts, sulfonated phenols and naphthols and their copolymers, melamine/glyoxal/glyoxylate/phenol/naphthol condensates; vegetable extractives, especially rhubarb, mimosa, peat, euphorbia, cassia, rose, tea, grape and saxifragea; sulfonated extractives, especially of mimosa wood; and bark extractives, such as oak, eucalyptus, fig, cedar, spruce, pine, walnut, mulberry and chestnut; and graft copolymers derived from thee extracts. Others include synthetic phenolic tanning agents (syntans) such as tanigan, tamol, ledertan, blancotan, basyntan, neosyn and nubuctan and phenolic compounds that cause melanization or sclerotization of proteins, especially catechol and dopamine amides, quinones, quinone methides, prenylated phenols and quinones and polymers derived from their oxidation, e.g., melanins and sclerotins, and the like.

Useful detergents include sodium dodecyl sulfate, sodium caprylate, sodium cholate, sodium decanesulfonic acid, sodium deoxycholate, sodium glycocholate, sodium deoxyglycocholate, sodium taurocholate, sodium taurodeoxycholate, cetylpyidinium chloride, dodecyltrimethyl annonium, CHAPS, CHAPSO, dioctyl solfosuccinate, alginic acid. Phenols useful to enhance detergent purification include t-butylphenol and bisphenols such as bisphenol A.

Removal of the impurities can be enhanced by adding a salt such as potassium chloride to the aqueous solution of the enzyme in an amount of about 1 to 10%. For certain protein fixatives such as the phenols which are not soluble in water, a small amount of a solvent such as an alcohol may be used to dissolve these fixatives in water.

Non-solvents of the peroxidase are used to force the enzyme to precipitate and enable its separation. Useful nonsolvents may be water miscible or water immiscible, however, they are preferably water miscible. Representative examples include acetone, isopropanol, n-propanol, methanol, and ethanol.

To purify the enzyme, peroxidase is added to water in an amount of about 400 units per ml water. When the protein fixative is used, it is generally added to the enzyme solution in an amount of about 1% to 10% based on weight of fixative to volume of enzyme (kg. to 1). Similar amounts of detergent are employed. The volume of the non-solvent which must be added to the enzyme solution to separate the enzyme will vary with the nature of the non-solvent but generally 1 to 10 volumes of non-solvent per volume of enzyme solution is required.

Any substrate previously used in horseradish peroxidase assays is useful in the present invention. The most common substrate is hydrogen peroxide.

Any indicator previously used in peroxidase assays should also be useful herein. The most common indicator is leuco dyes. Any suitable leuco dye can be used in the practice of this invention as long as it is capable of providing a detectable dye when oxidized in the presence of soy peroxidase and hydrogen peroxide. Examples of useful leuco dyes include, but are not limited to, imidazole derivatives such as those described in U.S. Pat. No. 4,089,747 and references noted therein, E.P. Application No. 122,641 (published Oct. 24, 1984)) and Jap. Patent Publication No. 58(1983)-045,557, and the triarylmethanes described, for example, in U.S. Pat. No. 4,670,385.

Certain additives may also be used to enhance the reaction rate of the peroxidase catalyzed oxidation of the leuco dye such as the phenols and anilines described in U.S. Pat. No. 4,828,983. Other additives commonly used such as buffers, surfactants, etc. may also be used in established amounts.

One or more reagents which react with the analyte to produce hydrogen peroxide can be used with the analytical composition of this invention in order to determine an analyte other than hydrogen peroxide. Suitable interactive compositions are known to one skilled in the art. For example, an interactive composition for the determination of uric acid includes uricase. An interactive composition for the determination of glucose includes glucose oxidase. An interactive composition for the determination of cholesterol includes cholesterol oxidase and cholesterol ester hydrolase.

The analytical composition of this invention can also be used to determine an antigens and the like using an enzyme-antibody conjugate or complex as described above. In one embodiment, that enzyme label is peroxidase. In other embodiments, the label is an enzyme other than peroxidase e.g. glucose oxidase, galactose oxidase, etc. that participates in the conversion of the analyte to hydrogen peroxide and the leuco dye to a detectable dye.

The analytical composition and method of this invention are adaptable to both solution and dry assays.

In a solution assay, the amount of the leuco dye (or other indicator) used will depend upon the extinction coefficient of the resulting dye. The appropriate amounts can be readily determined. Generally, the leuco dye is present in a concentration of at least about $4 \times 10^{-7}$ molar, and preferably from about $2 \times 10^{-4}$ molar. Similarly, peroxidase is present in an amount sufficient to oxidize the leuco dye to provide a detectable signal.

The antibodies are generally present in an amount of at lest about $10^{-8}$, and preferably from about $10^{-8}$ to about $10^{-3}$, molar.

The method of this invention can also be practiced with a dry analytical element. The simplest element can be composed of an absorbent carrier material, e.g. a thin sheet of a self-supporting absorbent or bibulous material, such as filter paper or strips, which contains an immobilized antibody. The element can be divided into two or more discrete zones with different compositions of the composition incorporated into individual zones of the carrier material. Such elements are known in the art as test strips, diagnostic elements, dip sticks, diagnostic agents and the like. See U.S. Pat. Nos. 3,992,158 and 4,258,001.

Useful absorbent carrier materials are soluble and maintain their structural integrity when exposed to water or biological fluids such as whole blood or serum. Useful elements can be prepared from paper, porous particulate structures, porous polymeric films, cellulose, glass fiber, woven and nonwoven fabrics (synthetic and nonsynthetic) and the like. Useful materials and procedures for making such elements are well known in the art as exemplified in U.S. Pat Nos. 3,092,465, 3,802,842, 3,915,647, 3,917,453, 3,936,357, 4,255,384, 4,270,920 and 4,312,834.

The porous spreading zone can be prepared from any suitable fibrous or non-fibrous material or mixtures of either or both as described in U.S. Pat. Nos. 4,292,272 (issued Sep. 29, 1981 to Kitajima et al), 3,992,158 (noted above), 4,258,001 (noted above) and 4,430,436 (issued Feb. 7, 1984 to Koyama et al) and Japanese Patent Publication 57(1982) 101760 (published Jun. 24, 1982).

In the elements of this invention, the components of the analytical composition are present in amounts which can be varied depending upon the same factors mentioned above in relation to solution assays. Generally, the leuco dye is present in an amount of at least about 10 I.U./m$^2$. Optimal levels can be readily determined by one skilled in the art.

An enzyme-antibody conjugate or the unconjugated antibody is preferably immobilized within the element prior to use, e.g. during manufacture. For example, it can be immobilized within the absorbent carrier material of the element. More particularly, it is immobilized within the porous spreading zone on a carrier material, such as glass or polymeric beads or other particles, resins,, fibers and the like. Useful carrier materials include a microorganism, such as Saphylococcus aureus, S. aureus-derived protein A, etc. Biotin-conjugated peroxidase bound to immobilized avidin is also useful. Alternatively, the porous absorbent carrier material can serve as the carrier material for immobilization.

A variety of different elements, depending on the method of assay, can be prepared in accordance with the present invention. Elements can be configured in a variety of forms, including elongated tapes of any desired width, sheets, slides or chips.

The invention is illustrated in more detail by the following non-limiting examples.

EXAMPLE 1

Method of harvesting soybean peroxidase: One kg of dry soybeans obtained from J. R. Kelly Company, Collinsville, Ill. was placed in a blender and homogenized in 5 l of water. The homogenate was filtered through four layers of cheesecloth and the filtrate saved. To 500 ml of the filtrate was added 75 ml of 10% tannic acid in 0.1M phosphate buffer. The mixture was centrifuged at 1500 Xg for 30 minutes and the supernatant saved. Protein in the supernatant was precipitated by pouring the supernatant into 3 volumes of acetone at room temperature. The acetone was decanted and the precipitate was dissolved in 500 ml of water. Protein contaminants were further removed by the addition of 2.5 ml of 50% ZnCl$_2$ in water. The Zn treated protein was centrifuged at 1500 Xg for 30 minutes and the supernatant was decanted. The supernatant was poured into 3 volumes of acetone to precipitate the Zn-treated protein. The acetone was decanted and the precipitate was dissolved in 100 ml of water and used as the source of soybean peroxidase enzyme.

EXAMPLE 2

Fifty pounds soybean seed hulls, obtained in ground form (untoasted) were mixed with 830 lbs. tap water (100 gallons) in a Cowles high speed emulsifier and stirred at 1,000 rpm for 15 minutes. The extract was filtered on a 34 tensile-bolt-cloth screen using a shaker. The filtrate was allowed to settle for 1 day. The supernatant was ultra-filtered using a 30,000 molecular weight cut-off polysulfone membrane, thereby concentrating peroxidase, 40-fold. The concentrate was assayed for peroxidase activity using the pyrogallol method outlined in the Sigma Chemical Company (horseradish) peroxidase bulletin. The concentrate showed 92 units per ml.

EXAMPLE 3

Harvesting and Purification of Soybean Peroxidase

Soybean hulls were obtained in a dry state. The hulls (50 g) were homogenized with a Ross Model 100L emulsifier (13,000 rpm) for 30 seconds in 500 ml tap water. The extract was frozen to −20° C. and then thawed and separated by centrifugation.

Whatman DE-52 (200 g) (a product of Whatman Bioscience Inc.) was added to 2 liters 5 mM sodium tetraborate, pH 10, containing the aqueous extract of ground soybean hulls. The solution was mixed for 20 minutes and filtered. The retentate (DE-52) was mixed with 2 liters 0.5M ammonium sulfate, stirred for 20 minutes and filtered. The ammonium sulfate concentration of the filtrate (DE-52 elution with ammonium sulfate) was adjusted to 3.9M and the pH was adjusted to 9. The filtrate was added to 400 g Whatman HB-1 hydrogen bonding media, stirred for 30 minutes and filtered. The retentate (HB-1) was mixed with 2 liters water, stirred for 30 minutes and filtered. The water elutant of HB-1 was concentrated by ultrafiltration on a 10,000 molecular weight cut off (MWCO) polysulfone membrane 10-fold. The concentrate was diluted to 50% (v/v) with acetone and centrifuged at 1,500 ×g for 15 minutes. The supernatant was diluted further to 75% (v/v) with acetone and centrifuged. The supernatant contained the final purified soybean peroxidase which was analyzed for specific activity (units per mg protein), heme content (absorbance ratio 403 nm / 275 nm), and purity by PEI ion exchange high performance liquid chromatography (HPLC). The pellet obtained from treatment at 75% acetone was resuspended in 1/5 the original volume in water and centrifuged at 1,500 ×g for 15 minutes. The supernatants from both the homogenate and the pellet generate a peroxidase suitable for diagnostic assays. An alternate purification is shown in Gilliken and Graham, Plant Physiology 96:214-220 (1991) where a diagnostic soybean seed hull peroxidase is purified to homogeneity.

EXAMPLE 4

Coupled Oxidation of Glucose and Pyrogallol 0.25 mg glucose oxidase from Finnsugar Biochemicals (30 glucose oxidase units), 2 nmoles, was mixed with 3 ml 10 mM pyrogallol in 20 mM potassium phosphate buffer, pH 6 and 0.3 mM in glucose. 0.1 ml of the soybean seed hull peroxidase concentrate (9 units) from Example 2 was mixed with the pyrogallol/glucose solution and the change in absorbance was measured at 420nm using a Shimadzu UV-160 spectro-photometer. The absorbance was measured for 40 seconds against a blank that did not contain peroxidase, but was otherwise of the same composition as the test sample. The oxidation of the glucose led to successful color development of pyrogallol. Omitting either enzyme led to no color development of pyrogallol, thus supporting the suggested reaction sequence.

Having described the invention in detail and by reference to preferred embodiments thereof, it will be apparent that modifications and variations are possible without departing from the scope of the invention defined in the appended claims.

What is claimed is:

1. An analytical composition comprising soybean peroxidase or a soybean peroxidase-antibody conjugate, an indicator which is capable of providing a detectable condition in the presence of peroxidase and hydrogen peroxide.

2. The composition of claim 1 wherein said indicator is a leuco dye.

3. The composition of claim 1 wherein said composition comprises soybean peroxidase and said indicator.

4. The composition of claim 1 wherein said composition comprises a soybean peroxidase-antibody conjugate and said indicator.

5. An analytical element comprising an adsorbent carrier material containing soybean peroxidase or a soybean peroxidase antibody conjugate.

6. A method for the determination of an analyte comprising the steps of contacting a sample of a liquid suspected of containing an analyte with soybean peroxidase or a soybean peroxidase-labeled antibody, an indicator which is capable of providing a detectable change in the presence of peroxidase and hydrogen peroxide, and determining said detectable change as a result of the presence of said analyte.

7. The method of claim 6 for the determination of an analyte other than hydrogen peroxide wherein said sample is also contacted with an interactive composition which is capable of reacting with said analyte to provide hydrogen peroxide.

8. A method for detecting an antigen which includes the steps of adding soybean peroxidase to a sample suspected of containing the antigen to be detected under conditions such that said peroxidase directly or indirectly bonds to said antigen via an antibody and adding a substrate for said peroxidase and an indicator to said sample under conditions such that said peroxidase and said substrate react with said indicator and produce a change which is an indication of the presence and/or amount of said antigen.

9. The method of claim 8 wherein said indicator is a leuco dye.

10. The method of claim 8 wherein said peroxidase is conjugated with said antibody.

11. The method of claim 8 wherein said method employs a first antibody which is specific to said antigen and a second antibody which bridges said first antibody to said peroxidase.

12. A soybean peroxidase-antibody conjugate.

13. A soybean peroxidase-antisoybean peroxidase antibody complex.

* * * * *